United States Patent [19]

Kukla

[11] Patent Number: 5,146,562
[45] Date of Patent: Sep. 8, 1992

[54] PATIENT CARE COMMUNICATION SYSTEM

[75] Inventor: Robert W. Kukla, Irving, Tex.

[73] Assignee: International Business Machines Corporation, Armonk, N.Y.

[21] Appl. No.: 764,003

[22] Filed: Sep. 23, 1991

Related U.S. Application Data

[62] Division of Ser. No. 771,320, Aug. 30, 1985, Pat. No. 5,101,476.

[51] Int. Cl.⁵ .............................................. G06F 15/16
[52] U.S. Cl. ............................ 395/200; 364/DIG. 2; 364/943; 364/943.44; 364/948.2; 364/948.21; 364/919
[58] Field of Search ... 364/200 MS File, 900 MS File; 395/200

[56] References Cited

U.S. PATENT DOCUMENTS 4,591,974 5/1986 Dornbush et al. .................. 364/200

Primary Examiner—Michael R. Fleming
Assistant Examiner—Debra A. Chun
Attorney, Agent, or Firm—Whitham & Marhoefer

[57] ABSTRACT

A patient care facility communication system with a plurality of communication terminals operatively coupled together for the transmission and receipt of messages, includes a program providing a message composition facility by which an operator may select one or more common items from a plurality of data screens, such as patient lists, address lists, work-item lists, and common message lists, to be included in messages frequently required to be sent for the efficient operation of the patient care facility.

15 Claims, 4 Drawing Sheets

PATIENT CARE COMMUNICATION SYSTEM

This application is a division of copending application Ser. No. 06/771,320, filed on Aug. 30, 1985, U.S. Pat. No. 5,101,476.

BACKGROUND OF THE INVENTION

This invention relates generally to communication systems and more particularly to a patient care system for use in hospitals and other patient care environments to provide a means for a highly efficient multiple-message and information communication facility As recent discoveries and developments in electronics and the physical sciences are applied to the medical profession, significant inroads are being made with regard to the diagnosis and treatment of a wide variety of human afflictions. Today it is possible to accurately measure many more variables which may be related to a patient's illness and to correlate those variables quickly and easily into a new meaningful patient diagnosis and/or statement of condition. Moreover, technological developments are being applied to all aspects of the hospital environment including radiology, laboratories, intensive care units, cardiology, nuclear medicine and even dietary units and prescription supplies. These advancements in the state of the art not only provide better and faster care for patients but also provide such improved care using fewer personnel.

The increased availability of patient-related data and information has created a need for improved communication systems throughout the many departments and laboratories in a hospital environment especially since much of the data is interrelated and data input from one source should be made known and coordinated with many other departments in a timely and efficient manner.

Many hospitals today have computerized communications systems in order to rapidly and accurately disseminate patient-related data to various communications stations throughout the patient care facility. Such systems include a main facility computer with communication terminals located throughout the facility at strategic locations. For example, there may be two or three nursing stations on each floor of a hospital with each station having a communication terminal and being responsible for the care and treatment of a predetermined number of patients in the immediate area. Additionally, each specified area, such as radiology, pharmacy, laboratory and nutrition, may have a separate terminal by which communications and test results may be sent to and/or received from any other specialized area or nursing station terminal.

Notwithstanding the relative sophistication of these communication systems, their efficiency has been limited since inputs are required from operating personnel and to the extent that the systems are complicated to format and/or operate (i.e. not "user friendly"), extensive specialized training or the hiring of specialist personnel may be required. Moreover, many such systems are "serially oriented" and can transmit or receive information or data related to only one patient at a time or to only one terminal at a time or with regard to only one treatment activity or "work-to-be-done" item. For example, in a typical communication system, the operator may type the entire message and perhaps for each destination. The message may contain patient names and locations, doctors' orders, and text. Such an arrangement requires an operator to repetitively input much of the same data with regard to each individual patient, destination, and/or treatment activity. Therefore, to the extent that these communication systems are serially oriented, duplicative of operator inputs are required and the full efficiency potential of the system is not being realized. In addition, with an improved communication system, highly-skilled patient care personnel would be able to devote more of their time to the care of patients and less time operating a communication terminal.

SUMMARY OF THE INVENTION

Accordingly, it is an object of the present invention to provide an improved patient care communication system which is menu driven for maximum user friendliness and which couples a general message transmission facility with a multiple selection of destinations, patients, work-to-be-done, and/or common message text displays or menus to substantially reduce the need for repetitive typing of the same input data in a patient care program utilized by hospitals and other patient care facilities. A message concerning one or a plurality of patients selected from a screen census can be transmitted selectively to a number of different departments or units within the hospital concerning work to be performed with respect to those patients Similarly, a worklist-oriented message including worklist items selected from a menu can be sent to selected units with respect to particular patients.

BRIEF DESCRIPTION OF THE DRAWINGS

A better understanding of the present invention may be had when the following specification is read with reference to the accompanying drawings in which.

DETAILED DESCRIPTION OF THE INVENTION

The present invention, as disclosed herein, is shown in a patient care operating environment, although the invention may be applied in various other fields of activity to effect more efficient and less time consuming communications among groups of users of computer-related communications and data processing equipment.

In the present example, a typical patient care facility includes many different functional areas such as a plurality of nursing units each with the responsibility for a number of patients, various laboratories and analysis areas such as blood analysis, and x-ray, together with specialized areas such as intensive care and coronary care. The present invention may be implemented in a system which includes a communications station at each of these locations. Typically, such a communications station would include a keyboard for entering data along with a display screen and a printer. The terminals may be so called "intelligent terminals" tied together by a network with a central computer for information processing or so called "dumb terminals" which totally rely on and are connected together by means of a central computer system.

In accordance with the present invention, the computer system is programmed in accordance with the flow charts illustrated in the attached figures to accomplish the communication of a common message referencing a plurality of patients to a number of predetermined addressees or to send worklist related messages to various units also referencing a plurality of patients in such units.

For example, it will be assumed that one of the nursing stations in the hospital has several patients who have been detained at the x-ray unit and are not available for the scheduled lunch. This could be a relatively common occurrence in many hospitals and in many cases a nurse would have to phone the dietary unit, wait to get a connection to the appropriate person, and advise that person of the situation. Alternatively, in some hospital systems this could be done electronically, but the user of the terminal for that particular nursing station would have to send individual messages with regard to each patient which would entail repetitive keying in of the same information for the several patients who are not available.

Figure 1:
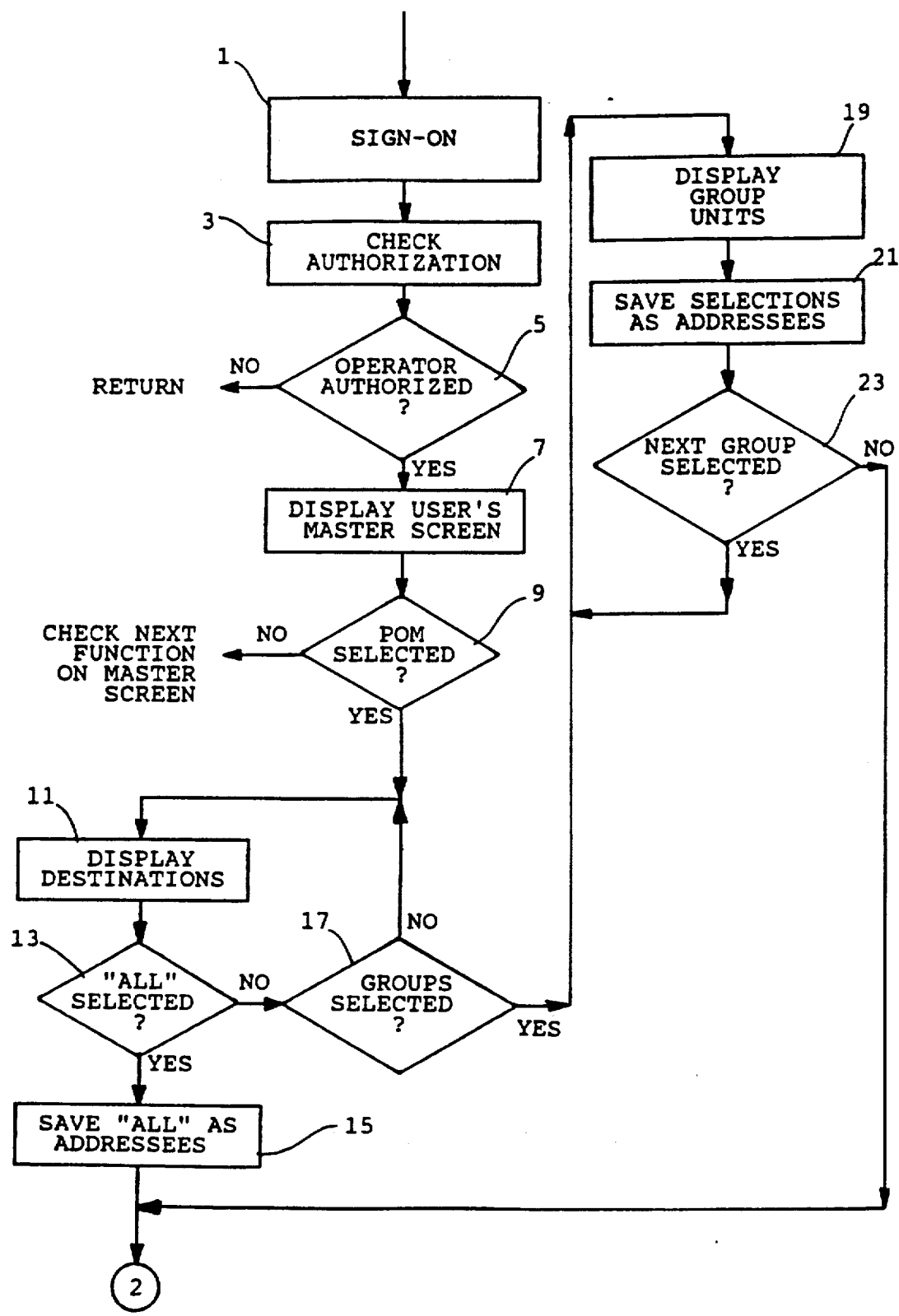
FIG. 1 is a functional flow diagram illustrating a portion of the methodology implemented in one embodiment of the present invention.

In the exemplary embodiment of the present invention, the terminal operator is assumed to already be "on-line", i.e., the user has already logged onto the system and entered a password which is automatically checked before the user is authorized to continue processing information on his particular terminal. That procedure is indicated in block 1 "SIGN ON" and block 3 "CHECK AUTHORIZATION" in FIG. 1. If the user does not have the proper sign-on procedure or does not have a valid password, the terminal is returned to the SIGN ON screen or may be directed to a HELP screen or other procedure required to effect proper initialization of the system terminal.

If the operator is authorized, the program proceeds past decision block 5 to display the user's MASTER SCREEN at block 7. The MASTER SCREEN generally displays a list of functions or operations available to the user which may be implemented by selecting the desired function. That selection process may be accomplished by means of keying in a number identified with the function on the screen or keying a program function ("PF") key, or by indicating the selected functions by using a light pen or any other input means generally known and available for such systems. Note: In the sample screens which follow, selection may be accomplished by a light pen or by typing. The "!" does not appear on the screen but is shown to indicate an immediate computer response when the light pen is used. The "?" is used to indicate a delayed computer response and is used when more than one selection is desired on the screen. If typing a selection, the operator would type an "X" in the field delimited by a "<" and ">". Typically those delimiters are not displayed on the screen.

A typical nursing UNIT SUPERVISOR MASTER screen is shown below:

| UNIT SUPERVISOR MASTER | <11/21/84 09:17> |
|---|---|
| Select one of the following: | |
| !03 Change Unit Patient Profiles | |
| !17 Display Patient Profiles (Unit) | |
| !21 Display Unit Worklist | |
| !39 Enter Results (Chart) for Unit | |
| !41 Identify Patient for Processing | |
| !55 Process Unverified Orders (Unit) | |
| !71 Send Message | |
| !72 Send Patient-Oriented Message | |
| Selection = = > <72> | |
| | SIGNOFF=S:< >: |
| <GENERAL HOSPITAL> | OPERATOR, SALLY> |

One of the functions on the MASTER screen is identified as "Send Patient-Oriented Message" (POM). If the Patient-Oriented Message function is not selected, the program will check the input to determine which function was selected on the master screen as indicated by the decision block 9. If the POM function has been selected, the program next displays the DESTINATION screen as indicated by block 11.

The DESTINATION screen as shown below is also menu-driven and designed to have the user identify the DESTINATIONS to which the message is to be sent.

| <SEND P.O. MESSAGE> MESSAGE DESTINATIONS <11/21/84 09:17> |
|---|
| If you wish to send a message to all destinations defined within each group, select 'All' for that group. If you wish to send a message to selected destinations in each group, select 'Selected' for that group. If you wish to transmit this message to all groups, select 'All Destinations'. |

| __Group__ | | |
|---|---|---|
| Nursing Units | < >? All | < >? Selected |
| Departments | < >? All | <X>? Selected |
| Other Areas | < >? All | < >? Selected |
| < >!All Destinations | | |
| | ENTER | |
| | !MASTER=PF12 | !RETURN=PF3 |
| <GENERAL HOSPITAL> | <OPERATOR, SALLY> | |

As hereinbefore noted, in general there are different types of possible destinations including one or more of the nursing units throughout the hospital, one or more of the various departments and/or other areas which cannot be categorized in either of the above two groups. The destination screen in the present example specifies an "All Destinations" input which, if selected by the user, will save all of the possible destinations in the destination file as addressees for the message to be sent as represented by blocks 13 and 15. On the "DESTINATIONS" screen, in addition to the "All" selection, the individual groups are identified as "Nursing Units", "Departments", and "other areas", and beside each group the user may select either an "All" or "Selected" input. For example, the user may select that the message should go only to Dietary Unit and, therefore, would check the "Selected" block on the menu. That choice is indicated at decision block 17 in FIG. 1. If the user wishes the message to go only to a selected department, the user would identify only the "Selected" block corresponding to the "Departments" group. At that point the program would display the individual department units comprising that group as shown in block 19. It should be noted that the list of destinations may be displayed from an existing file of destinations or an individually coded screen format. The department group units may include the various departments in the hospital which perform a service such as testing and analysis required in the care of patients such as laboratory, pharmacy, radiology, nuclear medicine, dietary, physical therapy, respiratory therapy, cytopathology, and various others depending upon the particular hospital environment. A typical DEPARTMENT DESTINATIONS screen is shown below:

exemplary LOCATION CENSUS screen is shown below:

```
<SEND P.O. MESSAGE>  LOCATION CENSUS    <11/21/84  09:17>
From Location: NE01 — NORTHEAST 01

Select one or more of the folowing:
        Room-Bd_____ Patient Name_____ Room-Bd_____ Patient Name_____
<x>?    0001-01 GLOVER, JOHN P.
<x>?    0001-02 HAHN, KERT M.
<  >?   0002-01 SMITH, SARAH
<  >?   0002-02 JONES, ANNE
             !PRINT=PF9    !ENTER       <  >! ALL PATIENTS THIS UNIT
        !<BACK=PF7    >   !<NEXT=PF8  >    !MASTER=PF12   !RETURN=PF3
                              <GENERAL HOSPITAL>    <OPERATOR, SALLY>
```

The Patient Census file is maintained when patients check into or out of the patient care facility and may be accessed by the terminals throughout the facility as needed. In addition, when the patient is assigned a room and bed number, that data is also stored and accessible. For example, when the Patient Census screen is displayed at block 25, the user may identify, by key input or light pen input or otherwise, the patients to which

```
<SEND P.O. MESSAGE>  DEPARTMENT DESTINATIONS    <11/21/84  09:17>

Select one or more of the following:
<  >? LAB — LABORATORY
<  >? PHR — PHARMACY
<  >? RAD — RADIOLOGY
<  >? CS — SUPPLIES
<  >? NM — NUCLEAR MEDICINE
<x>? DIET — DIETARY
<  >? PT — PHYSICAL THERAPY
<  >? RT — RESPIRATORY THERAPY
<  >? CYTO — CYTOPATHOLOGY
<  >? PATH — SURGICAL PATHOLOGY
             !ENTER
                      !MASTER=PF12     !RETURN=PF3
        <GENERAL HOSPITAL>      <OPERATOR, SALLY>
```

Figure 2:
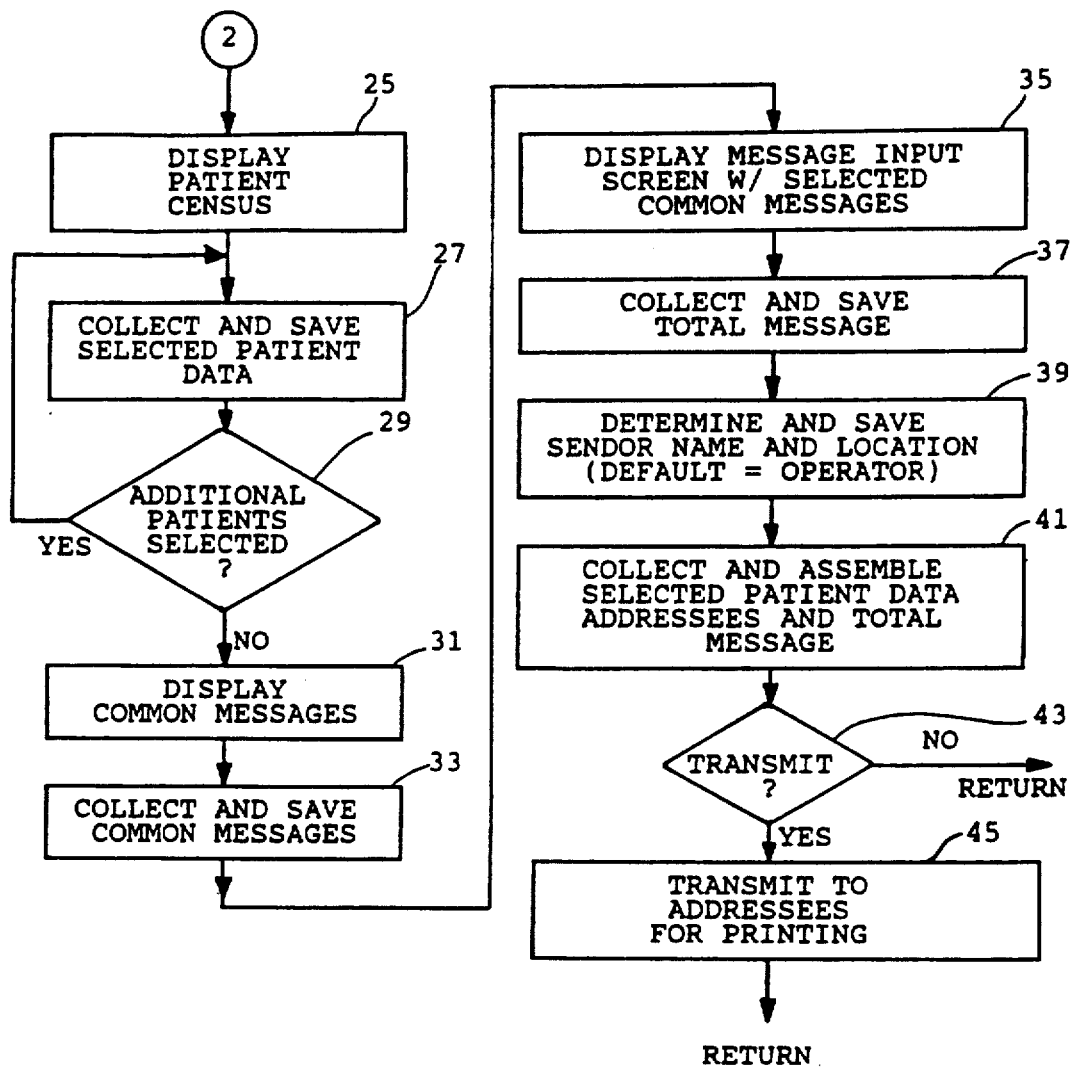
FIG. 2 is a continuation of FIG. 1.

In the present example, the user may indicate only the Dietary department on the menu and the program would save only the dietary location as the addressee for the message to be sent. After saving the selected addressees as indicated in block 21, the program would determine if any other groups were identified at decision block 23. If other groups were selected, the program would return to display the individual units in the other groups for selection and save those addressees as appropriate. If no additional groups were selected, the program returns to the mainstream flow which is continued at the top of FIG. 2. At that point, the program displays a PATIENT CENSUS for the user to identify one or more patients to which the message relates. An the message applies. A loop is set up in the program to Collect and Save the identities of the selected patients together with room and bed numbers as appropriate, as indicated by block 27 and decision block 29. After all of the patient selections have been collected and saved in the program, a common message screen is displayed as shown in block 31 in FIG. 2.

The COMMON MESSAGE screen as shown below, is designed to display a plurality of frequently occurring messages which are routinely sent and received during the normal operation of the patient care facility. It should be noted that the list of common messages may be displayed from an existing file of common messages or from an individually coded screen format.

```
<SEND P.O. MESSAGE>  COMMON MESSAGES    <11/21/84  09:17>

Select one of the following:
101 DELAY BREAKFAST
102 DELAY LUNCH
103 DELAY DINNER
104 RESUME BREAKFAST
105 RESUME LUNCH
106 RESUME DINNER
107 PROVIDE TRANSPORTATION
108 PATIENT(S) PREP'ED
109 SPECIMEN(S) COLLECTED
Selection ==><02>
             !CONTINUE=PF8    !MASTER=PF12    !RETURN=PF3
             <GENERAL HOSPITAL>       <OPERATOR, SALLY>
```

This screen is designed in accordance with the particular requirements of the patient care facility but may include common messages such as "DELAY BREAKFAST", "DELAY LUNCH", "DELAY DINNER", "PROVIDE TRANSPORTATION". In addition, the COMMON MESSAGE screen includes many common responses that are required to be sent in order to confirm that messages from other units have been received and have been acted upon. For example, the COMMON MESSAGE screen includes common response and/or confirmation messages such as "PATIENTS PREPARED", "SPECIMENS COLLECTED", etc.

It should also be noted that in the present program, each screen contains a function selection by which the user may exit at any time to return to the master menu in the event that there is no longer a need to send the message being prepared.

Returning to the present example, the user would check the selection specified as "DELAY LUNCH" in order to advise the dietary department to delay lunch for the identified patients. Once the patients have returned from the x-ray facility and are ready for lunch, the terminal operator can quickly and easily send an electronic message to "RESUME LUNCH" to that dietary department so that all of the patients returning to the nursing unit may enjoy a delicious and freshly prepared lunch at their convenience.

Also in accordance with the present invention, another example would allow the nursing unit to request that the transportation department take one or more specific patients to a specific department. This invention makes it very easy to compose these types of requests and provide hard-copy for the receiving destination.

Still another use is for a nursing unit to use the invention to create a type of worklist by sending itself a message such as: typing BATHE THE FOLLOWING PATIENTS after selecting patients from the census display.

After the user has selected the particular common messages which may be applicable, the program Collects and Saves those messages as indicated in block 33 and then Displays those Common Messages at block 35 in a format which allows the user to input unique data or specific messages if required. If such specific messages are keyed in, the program Collects and Saves the total message at 37 and then determines the name of the Sender of the message at 39. In the present example, the sender's identity is gleaned from the user file in the system unless the operator wishes to input another identification such as, for example, when one user is at a terminal in another department or unit.

At this point, the program Collects and Assembles the selected patient data, Addressees and Total Message to Display to the user as shown in 41. By keying a designated Transmit or Send key, the user can transmit the message as shown in decision block 43 at which time the message in total is transmitted to the selected addressees and automatically printed at those locations for proper handling as shown in block 45. If the message is not to be transmitted, the operator may make another selection by which the entire message may be cancelled and the user returned to the Main Menu screen. A typical PATIENT-ORIENTED MESSAGE screen, which would include selected Addressees and referenced patients, together with selected common messages and keyed messages, is shown below:

| PATIENT-ORIENTED MESSAGE | <11/21/84 09:17> |
|---|---|
| Attention: | DIETARY DEPARTMENT |
| From: | OPERATOR, SALLY |
| Signed-on: | OPERATOR, SALLY |
| Message Text: | |
| DELAY BREAKFAST | |

| Reference the following patient(s) from: NE01 — NORTHEAST 01 | | | |
|---|---|---|---|
| Room-Bd | Patient Name | Room-Bd | Patient Name |
| 0001-01 | GLOVER, JOHN P. | 0001-02 | HAHN, KERT M. |

Another example of the multi item message facility herein disclosed is illustrated with reference to FIGS. 3 and 4 with respect to facilities required of departments in the patient care facility. Many such departments have a need to send what are known as "worklist-oriented messagss" which relate more to services which must be performed by the departments in response to work orders placed by nurses or physicians in the facility. For example, departments need to know what has to be accomplished in the next several hours or within a certain period of time in order to assign those work items to personnel to insure the timely performance of the service. In some cases, the attending physician may require a blood sample analysis within one hour or immediately in emergency situations. In other cases where there is no immediate need, such analysis may be routinely accomplished in the normal time frame. In many cases the time requirement for sample analysis is critical and must be made known to the proper personnel and also the results of such analysis must be communicated to the appropriate station or terminal as soon as possible after they are known in order to determine or complete the most effective treatment program for the patient. Since the requirements for a department may differ from those of a nursing unit, normally the MASTER SCREEN for the department includes functions not found on the MASTER SCREEN for the nursing unit. One of the functions on the department MASTER MENU is designated "Send Worklist-Oriented Message" (WLO).

| DEPARTMENT MASTER | <11/21/84 09:17> |
|---|---|
| Select one of the following: | |
| !12 Display Basic Patient Data | !51 Process Orders |
| !14 Display Occurrences | !52 Process Orders for Patient |
| !15 Display Orders | !53 Process Orders for Unit |
| !16 Display Patient Profile | !56 Process Unverified Results |
| !19 Display Results | |
| !20 Display Department Worklist | !61 Record Performance Complete |
| !21 Display Unit Worklist | !62 Record Performance Incomplete |
| | !63 Renew Order |
| !31 Enter Charge or Credit | |
| !33 Enter Common Orders thid Dept | !71 Send Message |
| !36 Enter Orders | !73 Send Worklist-Oriented Message |
| Selection ==><73> | |

| -continued | | |
|---|---|---|
| DEPARTMENT MASTER | <11/21/84 | 09:17> |
| <GENERAL HOSPITAL> | SIGNOFF=S:< >:<br><OPERATOR, SALLY> | |

Figure 3:
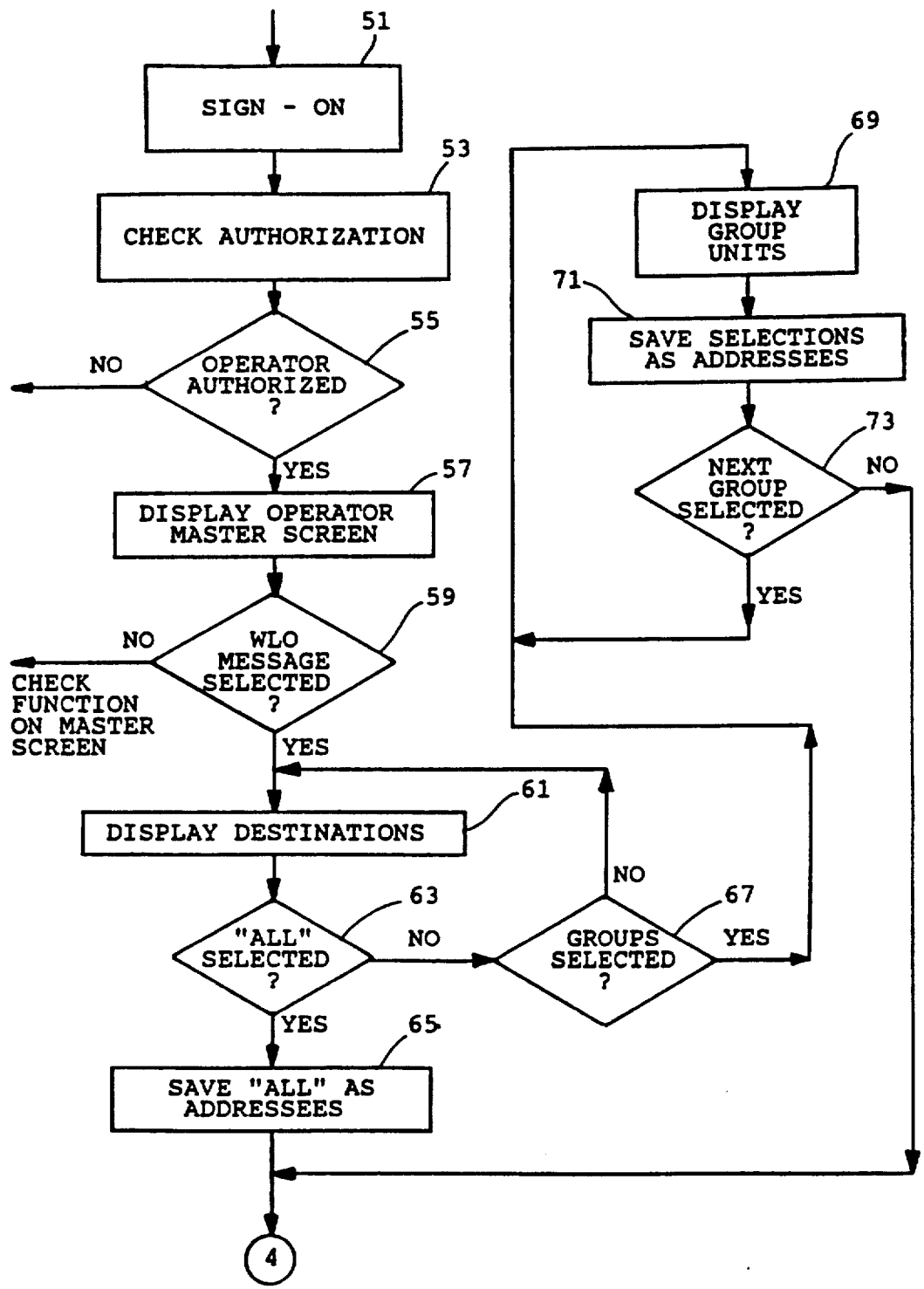
FIG. 3 is a functional flow diagram illustrating a portion of the methodology implemented in accordance with another embodiment of the present invention.
Figure 4:
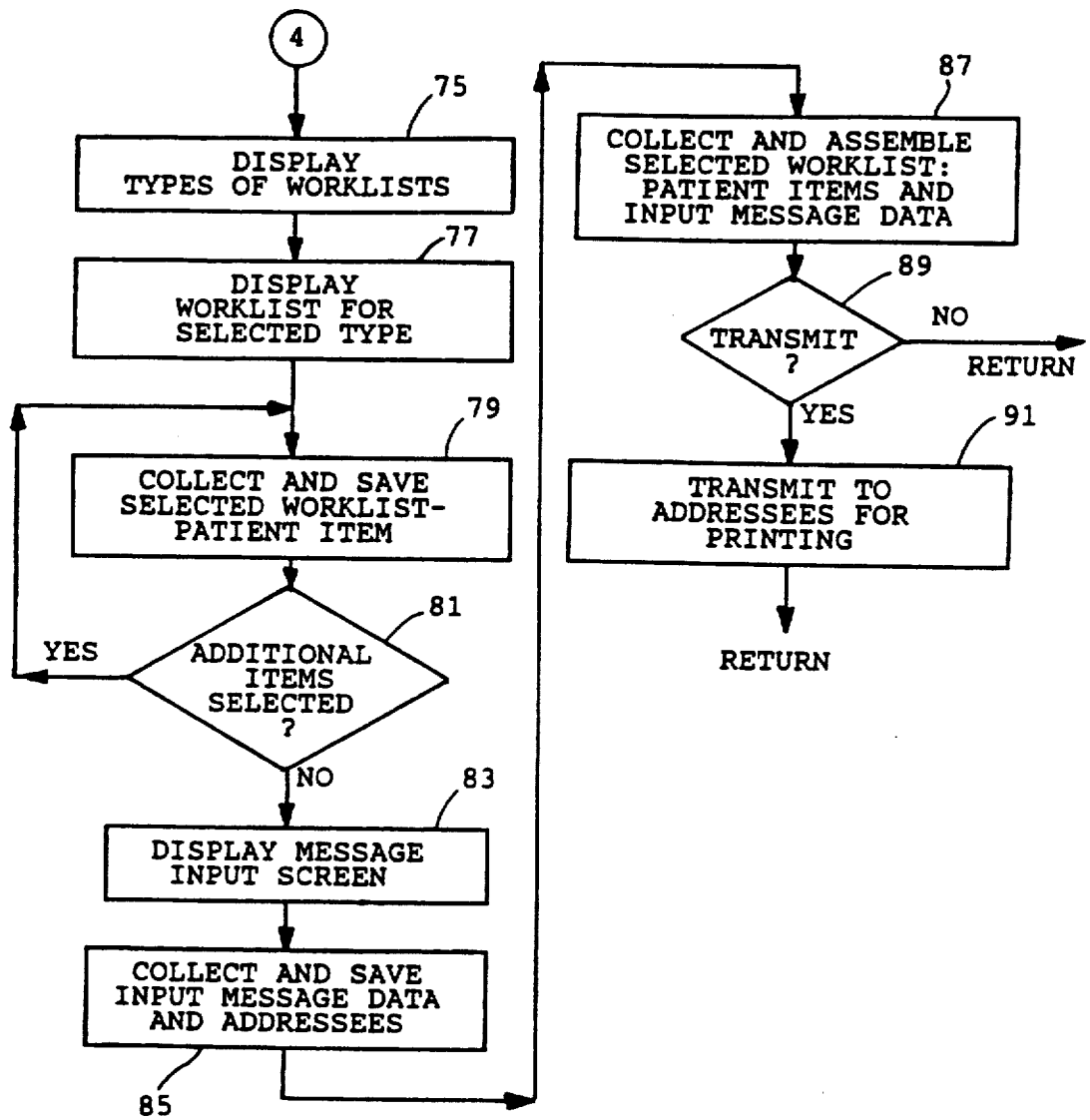
FIG. 4 is a continuation of FIG. 3.

The processing associated with the selection of that function is illustrated in FIG. 3 and continued in FIG. 4. In general, the "Sign On" process and DISPLAY OPERATOR MASTER SCREEN routines 51-57 are similar to those heretofore explained in connection with FIG. 1. When the operator within a department or laboratory selects the WLO function from the MASTER SCREEN at decision block 59, a DESTINATIONS screen 51 is presented and the routine for identifying and saving the Addressees of the message to be created, as shown in block 63-73 of FIG. 3, correspond to those heretofore explained in connection with blocks 13-23 of FIG. 1.

After the Addressees have been determined and saved, the program displays a screen entitled "TYPES OF WORKLISTS" as shown in block 75 of FIG. 4. The "Types of Worklist" items which are displayed on the WORKLIST screen include time-related items such as "Next Hour", "Next Four Hours", "Next Eight Hours", "Today 7-3", "Today 3-11", "Today 11-7", "Tomorrow", etc. Other items available for selection on the menu include "Uncompleted Orders", "Unverified Results", "Verified Results", etc. A typical WORKLIST TYPE screen for a clinical laboratory is shown below:

tion is saved in a file which is recalled in connection with the display of the worklist for a selected type of worklist. Accordingly, the DEPARTMENT WORKLIST display for the particular type of worklist includes information such as the referenced patient and the particular item ordered, with each item representing a separate service required of a single patient. If more than one service is required of a patient, then there will be a corresponding number of items in the displayed worklist. A typical DEPARTMENT WORKLIST screen is shown below:

| <SEND WLO MESSAGE> | | DEPARTMENT WORKLIST | | <11/21/84 | 10:15> |
|---|---|---|---|---|---|
| Select one or more of the following: | | | | Patient | |
| | Order | St_Req_ | _Perform_ | Name | St Loc |
| <X>? | CBC | OR R135798 | 112184 0900 | HAHN, KERT | IP NE01 |
| < >? | CBC | OR R254461 | 112184 0900 | DAVIS, ELSA | IP NW02 |
| < >? | HEMATOCRIT | OR R198763 | 112184 0900 | JONES, AMY | IP NE02 |
| <X>? | CBC | OR R192388 | 112184 1000 | LEE, DON | IP NE01 |
| < >? | WBC | OR R818772 | 112184 0900 | HANES, BOB | IP SW01 |
| | | | !PRINT=PF9 | !ENTER | !ALL OCCURRENCES=PF6 |
| | !<BACK=PF7 | > | !<NEXT=PF8 > | !MASTER=PF12 | !RETURN=PF3 |
| | | <GENERAL HOSPITAL> | | <TECHNOLOGIST, TOMMY> | |

All of the work items ordered by physicians with regard to particular patients are entered as separate items in the worklist. For example, the items designated "Within the Next Hour" were selected with the worklist "type". There may appear several requirements listed as separate items with regard to an individual patient. Patient Hahn, for example, may require both a blood analysis and an x-ray within the next hour and both of those items would be individually listed on clinical laboratory and radiology worklists, respectively. If the message were originating from the blood analysis lab, for example, the terminal user would select or identify the item designated as the blood analysis (CBC) for patient Hahn, since that is the only worklist

| <SEND WLO MESSAGE> LABORATORY WORKLIST TYPE <11/21/84 10:15><br>LOCATION: CLAB — CLINICAL LAB | |
|---|---|
| Select one of the following: | |
| SPECIMEN COLLECTION | OTHER |
| !01 Next Hour | !13 Uncompleted Orders |
| !02 Next 2 Hours | !14 Unresulted Orders |
| !03 Next 3 Hours | !15 Unverified Results |
| !04 Next 4 Hours | !16 Verified Results |
| !05 Next 5 Hours | |
| !06 Next 6 Hours | |
| !07 Next 7 Hours | |
| !08 Next 8 Hours | |
| !09 Today 7-3 | |
| !10 Today 3-11 | |
| !11 Today 11-7 | |
| !12 Tomorrow | |
| Selection = = > <02> | |
| | !MASTER=PF12    !RETURN=PF3 |
| <GENERAL HOSPITAL> | <TECHNOLOGIST, TOMMY> |

Once the types of worklists have been displayed and one has been selected, the particular worklist for the selected type is displayed as indicated at block 77. When physician orders are placed upon departments relative to the particular patients referenced, then that informaitem to which his message relates. After that selection the program Collects and Saves the selected Worklist-Patient Items at block 79 and determines whether additional items have been selected at 81. A loop is included to process any additional items and when the list is complete and no additional items have been selected and unprocessed, the program Displays a MESSAGE INPUT SCREEN at block 83. The MESSAGE INPUT SCREEN allows the operator to key in particular messages related to the particular Worklist Item and patient selected. That input message is Collected and Saved as indicated in block 85 together with the addressees previously selected by the operator. The program then Collects and Assembles the selected Worklist-Patient Items together with the particular message keyed in at block 87 and displays a WORKLIST-ORIENTED MESSAGE screen as shown below.

| WORKLIST-ORIENTED MESSAGE | | | < 11/21/84 | 10:15 > | |
|---|---|---|---|---|---|
| Attention: | | | NURSING UNIT | | |
| From: | | | TECHNOLOGIST, TOMMY | | |
| Signed-on: | | | TECHNOLOGIST, TOMMY | | |
| Message Text: | | | | | |
| SEND SPECIMENS | | | | | |
| Reference the following order(s) in department: CLAB — CLINICAL LAB | | | | | |
| Order | St | Req | Perform Date/Time | Patient | St Location |
| CBC | OR | R135798 | 112184 0900 | HAHN, KERT M. | IP NE01 |
| CBC | OR | R192388 | 112184 1000 | LEE, DON | IP NE01 |

The operator may then "send" the message to the Addressees for Printing at the location(s) as indicated in blocks 89 and 91. Again, if the operator decides not to transmit the message, the program will return him to the MASTER DEPARTMENT SCREEN to select other functions or compose other messages as required.

Outlines of the Patient-Oriented Message and Worklist-Oriented Message processes are shown below in high-level pseudocode which can be readily adapted to any system language for application to appropriate specific systems.

Send Patient-Oriented Message

1. Sign-On and Authorization
   1.1 Input Userid and Password
   1.2 Check Userfile
   1.3 Check Authorization
   1.4 Display Master Screen
2. Initiate Patient-Oriented Message Function
   2.1 Check for Selection
   2.2 Display Destination Screen
3. Process Destination Routine
   3.1 If "All" selected, save "All" as Addressees
   3.2 Else Display Group Units
      3.2.1 If "All" of Group selected, Save Group All
      3.2.2 If "Selected Units" designation is actuated, Save "Selected Unit" as Addressees
      3.2.3 Do until all Group Selections Saved
   3.3 Display Patient Census Screen from Census File
4. Select Patients referenced from Census File
   4.1 Save Patient Selected
   4.2 Do until all selected Patients Saved
   4.3 Display Common Message Screen
5. Select Common Messages
   5.1 Save Common Messages Selected
   5.2 Do Until all Selected Common Messages Saved
   5.3 Display Create Message Screen with Selected Common Messages
6. Input Specific Message
   6.1 Save keyed-in message with Selected Common Messages
7. Collect and Display Total Message including Saved Addresses, Referenced Patients, Common Messages and Specific Message.
8. Transmit and Print at Addressee locations.

Send Worklist-Oriented Message

1. Sign-On and Authorization
   1.1 Input Userid and Password
   1.2 Check Userfile
   1.3 Check Authorization
   1.4 Display Master Screen
2. Initiate Worklist-Oriented Message Function
   2.1 Check for Selection
   2.2 Display Destination Screen
3. Process Destination Routine
   3.1 If "All" selected, save "All" as Addressees
   3.2 Else Display Group Units
      3.2.1 If "All" of Group selected, Save Group All
      3.2.2 If "Selected Units" designation is actuated, Save Selected Unit as Addressees
      3.2.3 Do until all Group Selections Saved
   3.3 Display Type of Worklist Screen
4. Process Worklist-Oriented Message
   4.1 Display Worklist for Type Selected in 3.3
   4.2 Save Worklist-Patient items selected from 4.1
   4.3 Display Message Input Screen
5. Process Message Input
   5.1 Collect and Save Keyed Input Message Data
6. Collect and Display Total Message including Saved Addresses, Worklist-Patient items and Keyed Input Message
7. Transmit and Print at Addressee Locations.

With the present invention, it can be seen that through the use of carefully designed menus and sequential decision logic functions, recurring but often critical messages can be routinely and efficiently sent, processed and printed in order to optimize patient care resources and the quality of those resources. Although the present disclosure illustrates two examples of the multi-function message sending facility of the present invention, it is understood that the invention may be implemented in various other forms and in different applications and will provide an improved communication and work flow resource in many environments.

The actual programs required to implement the functions described herein will depend upon the particular system within which the present invention is implemented. The specific programs for the implemented systems are considered to be within the ability of a programmer having ordinary skill in the art after having reviewed the present specification, and the present disclosure is made in order to enable implementation of the present invention in the myriad of languages and systems presently available for various applications.

Although the present invention has been described in the context of the preferred embodiments thereof, it will be readily apparent to those skilled in the programming art that modifications and variations can be made therein without departing from the scope of the present invention as defined in the following claims.

The embodiments of the present invention in which an exclusive property or privilege is claimed are defined as follows:

1. A process for selectively and electronically composing and displaying for transmission messages at a communication station in a communications system which includes a plurality of display terminals connected to a central computer, said communication station being one of said display terminals and displaying screens containing reference data items stored in said central computer, the process comprising the steps of:
   displaying the reference data items in a screen on said communication station for selection by an operator;
   saving the reference data items selected by the operator in a temporary storage;
   composing a message made up of operator-selected items; and
   displaying the composed message for review and correction prior to transmission to another communications station in the communication system,
   displaying a second screen containing a list of possible addresses to whom the message may be sent for selection by the operator; and
   saving in said temporary storage the addresses selected by the operator from said second screen, said composed message also including the addresses selected from said second screen.

2. A process as in claim 1 further comprising the step of displaying as one of said screens a list of predefined commonly used messages as part of a screen format.

3. A process as in claim 1 further comprising the step of receiving at the communication station text input by the operator from a keyboard, said composed message being composed at least partially from said text entered by the operator from a keyboard.

4. A process as in claim 1 further comprising the steps of:
   displaying as one of said screens a list of predefined commonly used messages as part of the screen format; and
   receiving at the communication station text input by the operator from a keyboard, said message being composed at least partially from said text entered by the operator from a keyboard.

5. The process as in claim 1 and further including the steps of;
   displaying an input message screen for allowing the operator to input data other than the items on the screen; and
   saving in said temporary storage the data input by the operator, said composed message also containing the data input by the operator.

6. The process as in claim 1 wherein the step of displaying includes displaying in at least one of said screens data from existing files in the communications system.

7. The process as in claim 1 wherein the step of displaying includes displaying in at least one of said screens data from individually coded screen formats.

8. The process as in claim 1 further including the steps of:
   displaying a third screen, said third screen containing a plurality of data items for selection of one or more of said data items by the operator; and
   saving in said temporary storage the data items selected by the operator from the third screen, said composed message also containing the data items selected from the third screen.

9. The process as in claim 8 wherein the step of displaying the third screen includes displaying a list of predefined commonly used messages.

10. The process as in claim 8 and further including the steps of:
    displaying an input message screen for allowing the operator to input data other than the items on the screen; and
    saving in said temporary storage the data input by the operator, said composed message also containing the data input by the operator.

11. The process as in claim 10 and further including the steps of:
    displaying fourth screen containing items related to requests for services to be rendered for selection of one or more of said fourth screen items by the operator; and
    saving in said temporary storage the items selected by the operator from the fourth screen, said composed message also containing the items selected from the fourth screen.

12. The process as in claim 11 further comprising the step of receiving a user input selection from one of said screens by means of a light pen.

13. The process as in claim 11 and further including the steps of:
    receiving an operator input selection of one of the items from the first, second , third and fourth screens and data input one the message screen by means of a keyboard; and
    receiving an operator input selection of one of the items from the first, second, third and fourth screens by means of a light pen.

14. A process for selectively and electronically composing and displaying for transmission messages at a communication station in a communications systems which includes a plurality of display terminals connected to a central computer, said communication station being one of said display terminals and displaying screens containing reference data items stored in said central computer, the process comprising the steps of:
    displaying the reference data items in a screen on said communication station for selection by an operator;
    saving the reference data items selected by the operator in a temporary storage;
    composing a message made up of operator-selected items; and
    displaying the composed message for review and correction prior to transmission to another communications station in the.communication system,
    and further including the step of transmitting the composed message to selected destinations.

15. The process as in claim 14 further including the step of printing the composed message at printers located at the selected destinations.

* * * * *